(12) United States Patent
Gillis et al.

(10) Patent No.: US 7,320,681 B2
(45) Date of Patent: Jan. 22, 2008

(54) PATIENT MEDICAL TUBING ANCHOR AND METHOD

(75) Inventors: Gary A. Gillis, Ann Arbor, MI (US); Donald J. Propp, Dewitt, MI (US)

(73) Assignee: Tri-State Hospital Supply Corporation, Howell, MI (US)

( * ) Notice: Subject to any disclaimer, the term of this patent is extended or adjusted under 35 U.S.C. 154(b) by 672 days.

(21) Appl. No.: 10/781,431

(22) Filed: Feb. 18, 2004

(65) Prior Publication Data

US 2005/0182368 A1  Aug. 18, 2005

(51) Int. Cl.
*A61M 5/32* (2006.01)
(52) U.S. Cl. .......... 604/174; 128/DIG. 6; 128/DIG. 26
(58) Field of Classification Search ............ 604/93.01, 604/174, 180; 128/DIG. 6, DIG. 26
See application file for complete search history.

(56) References Cited

U.S. PATENT DOCUMENTS 4,397,647 A * 8/1983 Gordon ................. 604/180
4,849,226 A * 7/1989 Gale .................... 424/448

* cited by examiner

*Primary Examiner*—LoAn H Thanh
(74) *Attorney, Agent, or Firm*—Fildes & Outland, P.C.

(57) ABSTRACT

A medical tubing anchor includes a flexible anchor member and a base support having an adhesive side and a non-adhesive side. The flexible anchor member is a generally elongated rectangular solid having two elongated sides, two ends, a base, and a top. The anchor base of the anchor member is mounted on the base support non-adhesive side. The anchor member includes a plurality of stations defined by passageways transversing the anchor member and extending from the anchor member top towards the anchor member base. At least one tube holder having a generally cylindrical cross-section is located along the passageway in each of the stations for receiving medical tubing. The tube holders extend from one elongated side of the anchor member to the other elongated side. A keeper on the anchor member keeps medical tubing disposed in the stations from inadvertent release.

21 Claims, 3 Drawing Sheets

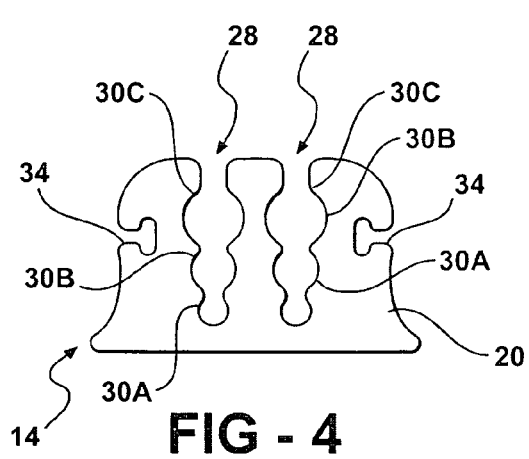
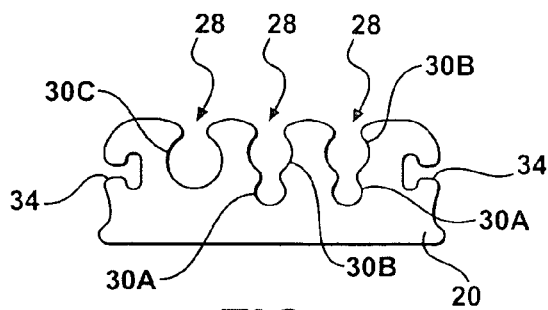
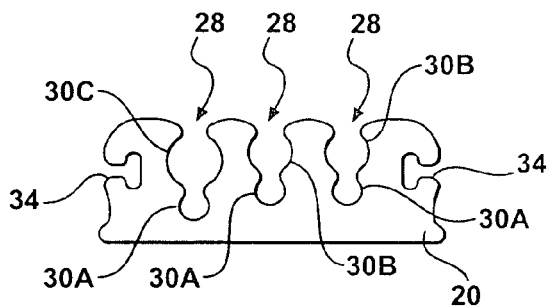
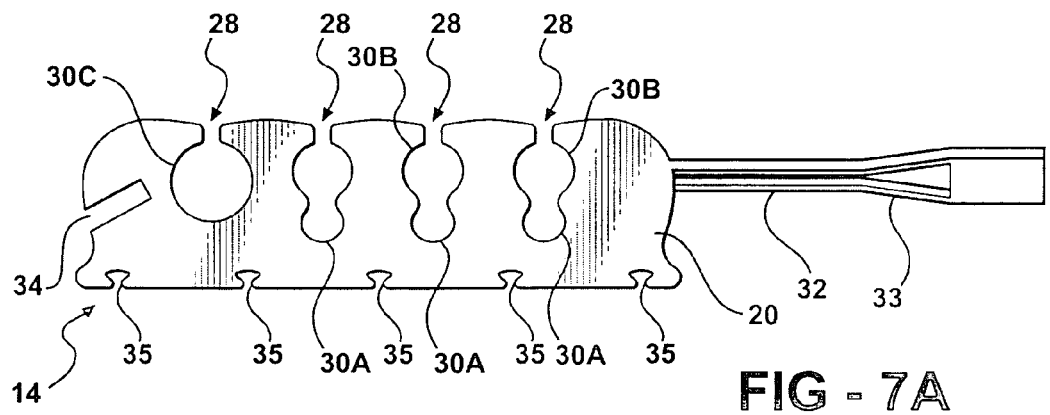
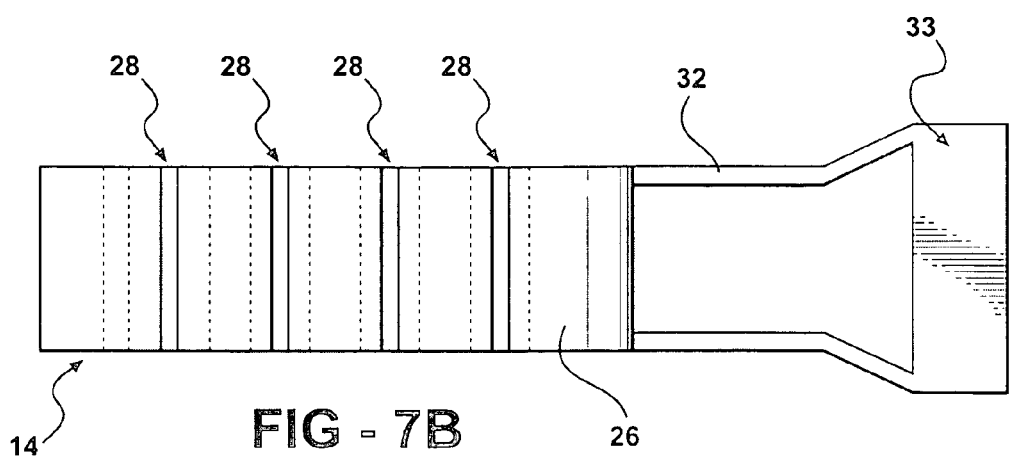

PATIENT MEDICAL TUBING ANCHOR AND METHOD

TECHNICAL FIELD

This invention relates to a medical tubing anchor for anchoring medical tubing, such as catheters, to the body of a patient, and more particularly to a medical tubing anchor that can securely anchor virtually any size and number of medical tubing to the body of a patient.

BACKGROUND OF THE INVENTION

It is known in the art relating to anchoring medical tubing, such as catheters, to anchor the tubing to the body of a patient by taping the tubing to the skin of a patient. It is also known to suture the tubing to the skin of a patient using various methods and apparatus. Both the taping method and the suture method are crude and do not provide a sufficient level of securement of the tubing to the patient. Sutures can easily tear out of the skin of the patient, thereby releasing the tubing. Tape more securely holds the tubing to a patient's body, but is still susceptible to coming loose depending on the strength of the adhesive used. The taping method is also undesirable in the likely case that more than one tube must be secured to a patient, because more of the patient's skin must be covered in tape to secure all of the tubing.

It is further known to use prefabricated anchoring devices that have an adhesive on one side and a mechanical anchor on the other side that locks a medical tube in place. These devices perform better than the taping or suturing methods, but still have shortcomings. For one, these devices can only accept one piece of tubing at a time. In other words, if more than one tube is used on a patient at a time, then multiple anchoring devices must be placed on the patient. Furthermore, most of these anchor devices have a low vertical profile (i.e., vertical height). This results in the tubing being anchored close to the patient's body. In some cases, this is desirable. In others, however, it is not. For example, if a patient is wearing a hospital gown and the tubing must be secured in an area under the gown, the gown will interfere with the tubing and/or the device.

SUMMARY OF THE INVENTION

The present invention provides a new and improved medical tubing anchor. The present medical tubing anchor is secure and will not tear away from a patient's skin as does medical tape or sutures. Further, the present medical tubing anchor can securely anchor multiple medical tubes of various sizes at one time. Moreover, the present invention can be worn with a hospital gown without the gown interfering with the anchor or the tubing.

A medical tubing anchor in accordance with the present invention includes a base support having an adhesive side and a non-adhesive side. The present invention further includes a flexible anchor member that is a generally elongated rectangular solid having two elongated sides, two ends, a base, and a top. The anchor base of the anchor member is mounted on the base support non-adhesive side. The anchor member further has a plurality of stations defined by passageways transversing the anchor member and extending from the anchor member top towards the anchor base. The stations are generally perpendicular to the elongated sides. At least one tube holder having a generally cylindrical cross-section is located along the passageway in each of the stations for receiving medical tubing. The tube holders extend from one elongated side to the other of the elongated sides. A keeper is retainable in the anchor member for keeping medical tubing disposed in the stations from inadvertent release.

In a preferred arrangement, the keeper may be an endless elastic member retainable in a slot located in each of the anchor member ends and the slots may be T-shaped. Alternatively, the keeper may be a band integrally molded with the anchor member at an end of the anchor member. In this embodiment, the keeper further may include a grasp tab integrally connected to the band. The keeper may be retainable in a slot located in the anchor member end opposite the keeper, the slot being configured to receive the grasp tab.

The anchor member may be comprised of a material having a hardness that measures between 20 A and 80 A durometer on Shore A scale; preferably 50 A durometer. This material may also be either a polyvinyl chloride material, a polyurethane material, a silicone material, or other non-rigid resin which exhibits friction when rubbed against the resins (typically PVC, PU, or silicone) that IV tubing and catheter tubing are made from. These careful choices of materials and durometer for the anchor member assure the anchor member has enough flexibility to accommodate different sizes of tubing and to assure openability for loading tubing into anchor member tube holders, while also assuring that there is friction between the anchor and the medical tubing to hold the tubing in place and prevent slipping. The base support may be comprised of a foam material chosen of adequate thickness and density to assure that a patient's natural body curvatures are accommodated and to assure patient comfort. The present invention may also include a siliconized release liner that generally corresponds in size and shape to the base support and that has a siliconized side that contacts the adhesive side of the base support. The present invention may further include a plurality of channels transversing the anchor member along the anchor base. The channels are adaptable to receive adhesive and create retention recesses for the adhesive used to mount the anchor member to the base support, thereby helping to overcome the difficulty of reliably bonding to high plasticizer, low durometer, soft anchor member material resin.

Optionally, at least one of the tube holders may be sized to accept an approximately 0.1 inch diameter tube. Further, at least one of the tube holders may be sized to accept an approximately 0.15 inch diameter tube. Furthermore, at least one of the tube holders may be sized to accept an approximately 0.2 inch diameter tube. The tube holders, however, may be larger than 0.2 inches or smaller than 0.1 inches in diameter and/or may be any nominal diameter desired to create friction with any tubing to be held.

In a preferred arrangement, the anchor member of the present invention may include four stations. Three of the stations may each include a tube holder that is sized to accept an approximately 0.1 inch diameter tube and a tube holder that is sized to accept an approximately 0.15 inch diameter tube. In each station, the 0.1 inch tube holder may be located below the 0.15 inch tube holder. The fourth station may include a tube holder that is sized to accept an approximately 0.2 inch diameter tube.

In an alternative preferred arrangement, the present invention may include a tube holder that is sized to accept an approximately 0.1 inch diameter tube, a tube holder that is sized to accept an approximately 0.15 inch diameter tube, and a tube holder that is sized to accept an approximately 0.2 inch diameter tube located together in at least one of the stations of the anchor member. The 0.1 inch tube holder may be located below the 0.15 inch tube holder and the 0.15 inch tube holder may be located below the 0.2 inch tube holder. The anchor member may have two stations and three tube holders per station.

In another alternative preferred arrangement, the present invention may include two tube holders that are sized to accept an approximately 0.1 inch diameter tube and a tube holder that is sized to accept an approximately 0.15 inch diameter tube located together in at least one of the stations of the anchor member. The 0.1 inch tube holders may be located below the 0.15 inch tube holder. The anchor member may have two stations and three tube holders per station.

In another alternative preferred arrangement, the present invention may include a tube holder that is sized to accept an approximately 0.1 inch diameter tube and a tube holder that is sized to accept an approximately 0.15 inch diameter tube located in each of the stations of the anchor member, the 0.1 inch tube holder being located below the 0.15 inch tube holder. The anchor member may have three stations and two tube holders per station.

A method of anchoring medical tubing to the body of a patient includes the steps of providing a base support, the base support having an adhesive side and a non-adhesive side; a flexible anchor member, the anchor member being a generally elongated rectangular solid having two elongated sides, two ends, a base, and a top; the anchor base of the anchor member being mounted on the base support non-adhesive side; the anchor member having a plurality of stations defined by passageways transversing the anchor member and extending from the anchor member top towards the anchor member base, the stations being generally perpendicular to the elongated sides; at least one tube holder having a generally cylindrical cross-section is located along the passageway in each of the stations for receiving medical tubing, the tube holders extending from one elongated side to the other of the elongated sides; and a keeper retainable in/on the anchor member for keeping medical tubing disposed in the stations from inadvertent release. The method further includes the steps of placing the adhesive side of the base support onto the body of a patient, removing the keeper from the anchor member, inserting at least one medical tube into an empty tube holder of the anchor member, and retaining the keeper in the anchor member.

These and other features and advantages of the invention will be more fully understood from the following detailed description of the invention taken together with the accompanying drawings.

BRIEF DESCRIPTION OF THE DRAWINGS

In the drawings:

FIG. 4 is a front view of an anchor member of an alternative embodiment of a medical tubing anchor in accordance with the present invention;

FIG. 5 is a front view of an anchor member of another alternative embodiment of a medical tubing anchor in accordance with the present invention;

FIG. 6 is a front view of an anchor member of another alternative embodiment of a medical tubing anchor in accordance with the present invention;

FIG. 7A is a front view of an anchor member of another alternative embodiment of a medical tubing anchor in accordance with the present invention;

FIG. 7B is a top view of the anchor member of FIG. 7A; and

DETAILED DESCRIPTION OF THE INVENTION

Figure 1:
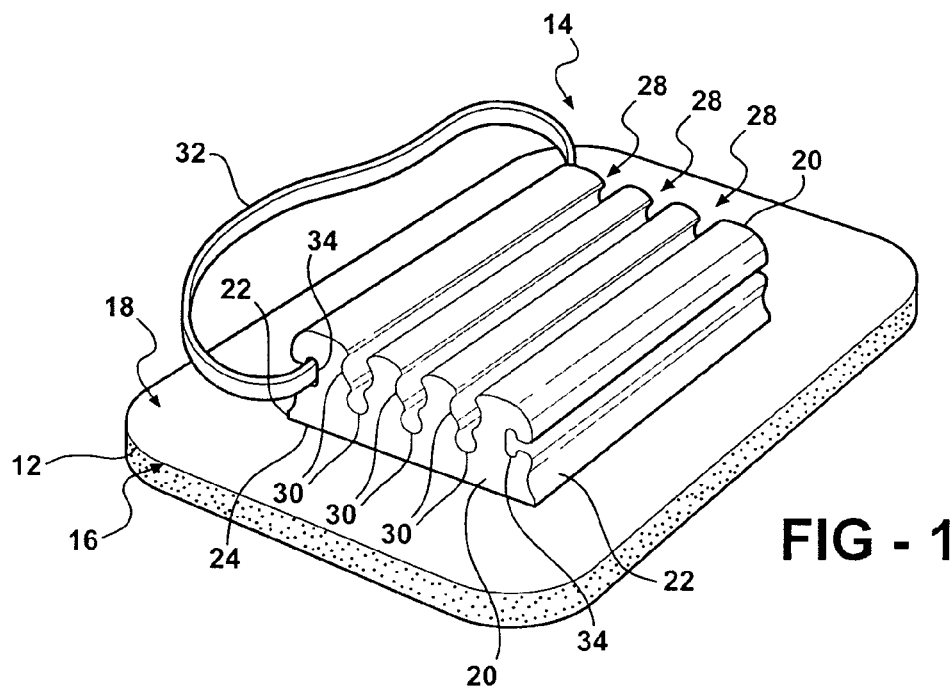
FIG. 1 is a perspective view of a medical tubing anchor in accordance with the present invention.

Referring now to the drawings in detail, numeral 10 generally indicates a medical tubing anchor in accordance with the present invention that provides for secure anchoring of multiple number and sizes of medical tubes to the body of a patient.

FIG. 1 illustrates an embodiment of a medical tubing anchor 10 which includes a base support 12 and a flexible anchor member 14. The base support 12 has an adhesive side 16 and a non-adhesive side 18. The base support 12 has a medical grade adhesive such as an acrylic adhesive applied to the adhesive side 16. The base support 12 may be comprised of a foam material chosen of adequate thickness and density to assure that a patient's natural body curvatures are accommodated and to assure patient comfort. This material gives the base support 12 sufficient adhesive surface area to reliably support the medical tubing anchor 10 while also giving the base support flexibility to fit the contours of the body of a patient. The flexible anchor member 14 is a generally elongated rectangular solid having two elongated sides 20, two ends 22, an anchor base 24, and a top 26. The height of the anchor member 14 defined by the elongated sides 20 and the ends 22 allows the anchor member 14 to sit outside of a slit in a medical gown, for example, while the base support 12 rests underneath the gown. The anchor member 14 may be comprised of a material that has a hardness that measures in the range of 20 A-80 A durometer on Shore A scale, preferably 50 A durometer. This material may also be either a polyvinyl chloride material, a polyurethane material, a silicone material, or other non-rigid resin which exhibits friction when rubbed against the resins (typically PVC, PU, or silicone) that IV tubing and catheter tubing are made from. These materials have properties such that there is a high level of friction between the anchor member 14 and the medical tubing to hold the tubing in place and to prevent slipping. These materials also assure that the anchor member 14 is sufficiently flexible to assure openability for loading medical tubing and to allow for the reception and anchoring of various sizes of medical tubes.

The anchor base 24 of the anchor member 14 is mounted on the base support non-adhesive side 18. The anchor member 14 has a plurality of stations 28 defined by passageways that transverse the anchor member and extend from the anchor member top 26 towards the anchor base 24. The stations 28 are generally perpendicular to the elongated sides 20. Tube holders 30 that have a generally cylindrical cross-section are located along the passageway in each of the stations 28 and extend from one elongated side 20 to the other of the elongated sides 20. The tube holders 30 enable the reception and anchoring of medical tubing (not shown).

A keeper 32 is retainable in the anchor member 14 for keeping medical tubing disposed in the stations 28 from inadvertent release.

In this embodiment, the keeper 32 is an endless elastic member retainable in a slot 34 in each of the anchor member ends 22 and the slots 34 are defined by T-shaped grooves. The T-shape of the slots 34 allows for retention of the keeper 32. The keeper 32 is inserted into the "bottom" of the T of the slot 34 and secured by the "top" of the T of the slot 34.

Figure 2A:
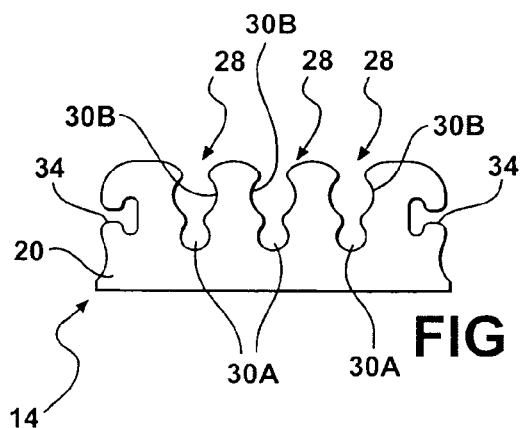
FIG. 2A is a front view of an anchor member of an embodiment of a medical tubing anchor in accordance with the present invention.
Figure 2B:
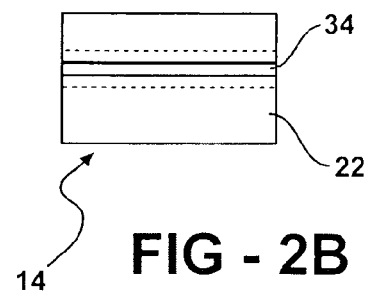
FIG. 2B is a side view of the anchor member of FIG. 2A.

FIGS. 2A and 2B show an arrangement of stations 28 and tube holders 30 in an anchor member 14 in accordance with an embodiment of the medical tubing anchor 10. FIG. 2A is a front view of the anchor member 14 showing an elongated side 20. The slots 34 are visible at edges of the elongated side 20. The slots 34 are also visible in FIG. 2B, which shows the position of the slots 34 in the ends 22 of the anchor member 14. The anchor member 14 includes three stations 28, and two tube holders 30 are in each station 28. Tube holders 30A are sized to accept an approximately 0.1 inch diameter medical tube and can accept tubes in the range of about 0.085 inches in diameter to 0.11 inches in diameter. Tube holders 30B are sized to accept an approximately 0.15 inch diameter medical tube and can accept tubes in the range of about 0.14 inches in diameter to 0.165 inches in diameter. Tube holders 30A are located below tube holders 30B. This embodiment is useful to anchor catheters to a patient after the patient has left the operating room.

Figure 3A:
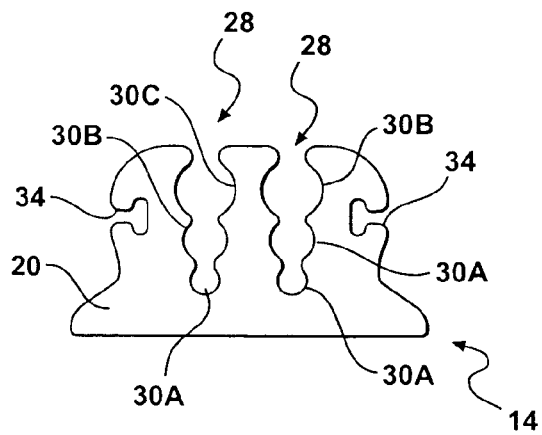
FIG. 3A is a front view of an anchor member of an alternative embodiment of a medical tubing anchor in accordance with the present invention.
Figure 3B:
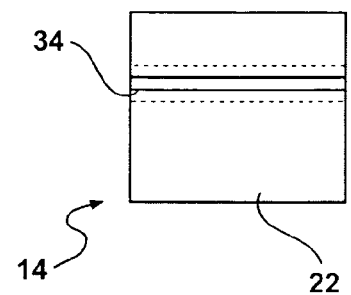
FIG. 3B is a side view of the anchor member of FIG. 3A.

FIGS. 3A and 3B show another arrangement of stations 28 and tube holders 30 in an anchor member 14 in accordance with an embodiment of the medical tubing anchor 10. FIG. 3A is a front view of the anchor member 14 showing an elongated side 20. The slots 34 are visible at edges of the elongated side 20. The slots 34 are also visible in FIG. 3B, which shows the position of the slots 34 in the ends 22 of the anchor member 14. The anchor member 14 includes two stations 28, and three tube holders 30 are in each station 28. Tube holders 30A are sized to accept an approximately 0.1 inch diameter medical tube and can accept tubes in the range of about 0.085 inches in diameter to 0.11 inches in diameter. Tube holders 30B are sized to accept an approximately 0.15 inch diameter medical tube and can accept tubes in the range of about 0.14 inches in diameter to 0.165 inches in diameter. Tube holder 30C is sized to accept an approximately 0.2 inch diameter medical tube and can accept tubes in the range of about 0.17 inches in diameter to 0.21 inches in diameter. Tube holders 30B are located above tube holders 30A and tube holder 30C is located above tube holder 30B. This embodiment is useful to anchor central venous catheters (CVC), Swan-Ganz catheters, introducer sheaths with side port tubing, etc., to a patient in the operating room and the intensive care unit.

FIGS. 4 through 6 illustrate further alternative arrangements of stations 28 and tube holders 30 in an anchor member 14 in accordance with embodiments of the medical tubing anchor 10. FIG. 4 is a front view of the anchor member 14 showing an elongated side 20. The slots 34 are visible at edges of the elongated side 20. The anchor member 14 includes two stations 28, and three tube holders 30 are in each station 28. Tube holders 30A are sized to accept an approximately 0.1 inch diameter medical tube and can accept tubes in the range of about 0.085 inches in diameter to 0.11 inches in diameter. Tube holders 30B are sized to accept an approximately 0.15 inch diameter medical tube and can accept tubes in the range of about 0.14 inches in diameter to 0.165 inches in diameter. Tube holders 30C are sized to accept an approximately 0.2 inch diameter medical tube and can accept tubes in the range of about 0.17 inches in diameter to 0.21 inches in diameter. Tube holders 30A are located below tube holders 30B and tube holders 30B are located below tube holders 30C.

FIG. 5 is a front view of the anchor member 14 showing an elongated side 20. The slots 34 are visible at edges of the elongated side 20. The anchor member 14 includes three stations 28, and two tube holders 30A, 30B are in two of the stations 28 while one tube holder 30C is in one of the stations 28. Tube holders 30A are sized to accept an approximately 0.1 inch diameter medical tube and can accept tubes in the range of about 0.085 inches in diameter to 0.11 inches in diameter. Tube holders 30B are sized to accept an approximately 0.15 inch diameter medical tube and can accept tubes in the range of about 0.14 inches in diameter to 0.165 inches in diameter. Tube holder 30C is sized to accept an approximately 0.2 inch diameter medical tube and can accept tubes in the range of about 0.17 inches in diameter to 0.21 inches in diameter. Tube holders 30A are located below tube holders 30B; tube holder 30C is located alone in one of the stations 28.

FIG. 6 is a front view of the anchor member 14 showing an elongated side 20. The slots 34 are visible at edges of the elongated side 20. The anchor member 14 includes three stations 28, and two tube holders 30 are in each station 28. Tube holders 30A are sized to accept an approximately 0.1 inch diameter medical tube and can accept tubes in the range of about 0.085 inches in diameter to 0.11 inches in diameter. Tube holders 30B are sized to accept an approximately 0.15 inch diameter medical tube and can accept tubes in the range of about 0.14 inches in diameter to 0.165 inches in diameter. Tube holder 30C is sized to accept an approximately 0.2 inch diameter medical tube and can accept tubes in the range of about 0.17 inches in diameter to 0.21 inches in diameter. Tube holders 30B are located above two of tube holders 30A and tube holder 30C is located above one of tube holders 30A.

FIGS. 2 through 6 demonstrate the wide range of potential applications of the present invention. FIGS. 2 through 6 show five possible arrangements of stations 28 and tube holders 30. Numerous other combinations of stations 28 and tube holders 30 are possible. These arrangements are capable of accommodating virtually all conceivable combinations of single lumen, double lumen, and triple lumen CVC jugular catheters, Swan-Ganz TD catheters, and introducer sheaths with side port tubing. In sum, FIGS. 2 through 6 illustrate that the present invention can be designed to accommodate any number and size of medical tubing.

FIG. 7A is a front view of an alternative embodiment of the anchor member 14 showing an elongated side 20. FIG. 7B is a top view of the embodiment shown in FIG. 7A. In this embodiment, the anchor member 14 includes a plurality of channels 35 transversing the anchor member 14 along the anchor base 24. The channels 35 are adapted to receive adhesive and create retention recesses for the adhesive used to mount the anchor member 14 to a base support when the anchor member 14 is mounted to a base support. This helps to overcome the difficulty of reliably bonding to high plasticizer, low durometer, soft anchor member material resin. In this embodiment, the keeper 32 is an elastic band integrally molded with the anchor member 14 at an end 22 of the anchor member 14. The keeper 32 further includes a grasp tab 33 integrally connected to the elastic band. The keeper 32 may be retainable in a slot 34 located in the anchor member end 22 opposite the keeper 32, the slot 34 being configured to receive the grasp tab 33.

The anchor member 14 includes four stations 28, and two tube holders 30A, 30B are in three of the stations 28 while one tube holder 30C is in the fourth station 28. Tube holders 30A are sized to accept an approximately 0.1 inch diameter medical tube and can accept tubes in the range of about 0.085 inches in diameter to 0.11 inches in diameter. Tube holders 30B are sized to accept an approximately 0.15 inch diameter medical tube and can accept tubes in the range of about 0.14 inches in diameter to 0.165 inches in diameter. Tube holder 30C is sized to accept an approximately 0.2 inch diameter medical tube and can accept tubes in the range of about 0.17 inches in diameter to 0.21 inches in diameter. Tube holders 30B are located above tube holders 30A.

Figure 8:
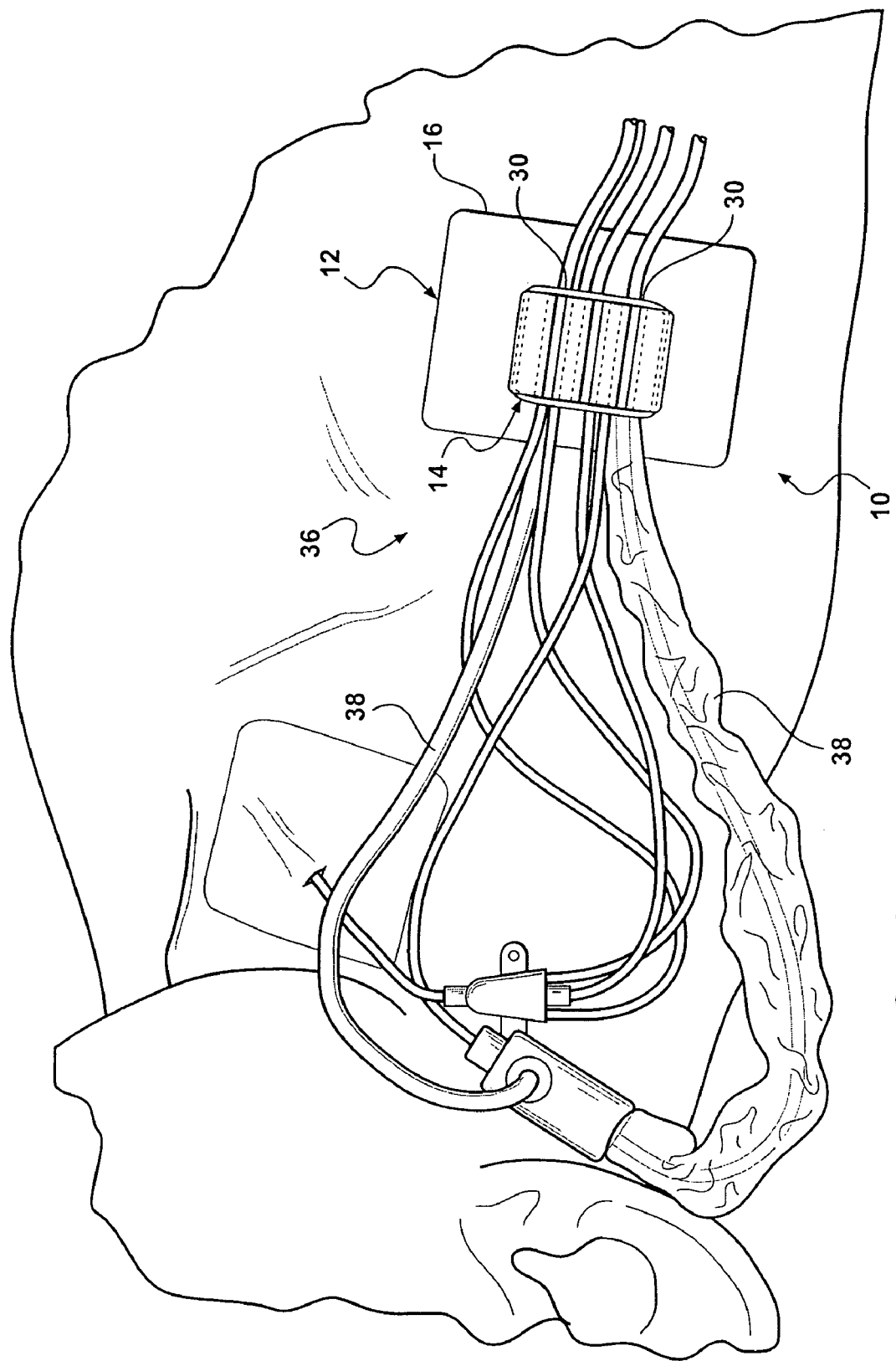
FIG. 8 is an environmental view of a medical tubing anchor in accordance with the present invention anchoring medical tubing to the body of a patient.

FIG. 8 is an environmental view of a medical tubing anchor 10 in accordance with the present invention anchoring medical tubing to the body of a patient. The adhesive side 16 of the base support 12 of the medical tubing anchor 10 was placed onto the body of a patient 36 at a desired location on the body of the patient 36. This secures the medical tubing anchor 10 to the patient 36. The keeper 32 is then opened from one end of the anchor member 14. When the keeper 32 is opened from the anchor member 14, the tube holders 30 are in an open position and ready to receive medical tubing 38. The medical tubing 38 is then inserted into empty tube holders 30 of the anchor member 14, one tube per tube holder 30. The keeper 32 is then closed/retained in the anchor member 14 to lock the anchor member 14.

Although the invention has been described by reference to a specific embodiment, it should be understood that numerous changes may be made within the spirit and scope of the inventive concepts described. Accordingly, it is intended that the invention not be limited to the described embodiment, but that it have the full scope defined by the language of the following claims.

What is claimed is:

1. A medical tubing anchor for anchoring a plurality of medical tubing comprising:
    a base support, said base support having an adhesive side and a non-adhesive side;
    a flexible anchor member, said anchor member being a generally elongated rectangular solid having two elongated sides, two ends, a base, and a top;
    said anchor base of said anchor member being mounted on said base support non-adhesive side;
    said anchor member having a plurality of stations defined by passageways transversing said anchor member and extending from said anchor member top towards said anchor member base;
    at least one tube holder having a generally cylindrical cross-section is located along said passageway in each of said stations for receiving medical tubing, said at least one tube holder extending from one elongated side to the other of said elongated sides; and
    a keeper on said anchor member for keeping medical tubing disposed in said stations from inadvertent release;
    each of said at least one tube holder of each said station being capable of receiving separate medical tubing, whereby said medical tubing anchor anchors a plurality of medical tubing.

2. The medical tubing anchor of claim 1, wherein said keeper is an endless elastic member retainable in a slot located in each of the anchor member ends.

3. The medical tubing anchor of claim 2, wherein said slots are T-shaped.

4. The medical tubing anchor of claim 1, wherein said keeper is an elastic member integrally formed as part of said flexible anchor member at an end of said anchor member.

5. The medical tubing anchor of claim 4, wherein said keeper further comprises a grasp tab integrally connected to said elastic member, said grasp tab being retainable in a slot located in said anchor member end opposite said keeper.

6. The medical tubing anchor of claim 1, further comprising a siliconized release liner having a siliconized side contacting said adhesive side of said base support; said release liner generally corresponding in size and shape to said base support.

7. The medical tubing anchor of claim 1, further comprising a plurality of channels transversing said anchor member along said anchor base, said channels being adaptable to receive adhesive used to mount said anchor member to said base support.

8. The medical tubing anchor of claim 1, wherein said anchor member comprises a material having a hardness between 20 A and 50 A durometer.

9. The medical tubing anchor of claim 8, wherein said material is one of a polyvinyl chloride material, a polyurethane material, and a silicone material.

10. The medical tubing anchor of claim 1, wherein said base support is comprised of a foam material.

11. The medical tubing anchor of claim 1, wherein at least one of said tube holders is sized to accept an approximately 0.1 inch diameter tube.

12. The medical tubing anchor of claim 1, wherein at least one of said tube holders is sized to accept an approximately 0.15 inch diameter tube.

13. The medical tubing anchor of claim 1, wherein at least one of said tube holders is sized to accept an approximately 0.2 inch diameter tube.

14. The medical tubing anchor of claim 1, wherein a tube holder that is sized to accept an approximately 0.1 inch diameter tube, a tube holder that is sized to accept an approximately 0.15 inch diameter tube, and a tube holder that is sized to accept an approximately 0.2 inch diameter tube are located together in at least one of said stations of said anchor member, the 0.1 inch tube holder being located below the 0.15 inch tube holder and the 0.15 inch tube holder being located below the 0.2 inch tube holder.

15. The medical tubing anchor of claim 1, wherein two tube holders that are sized to accept an approximately 0.1 inch diameter tube and a tube holder that is sized to accept an approximately 0.15 inch diameter tube are located together in at least one of said stations of said anchor member, the 0.1 inch tube holders being located below the 0.15 inch tube holder.

16. The medical tubing anchor of claim 1, wherein a tube holder that is sized to accept an approximately 0.1 inch diameter tube and a tube holder that is sized to accept an approximately 0.15 inch diameter tube are located in each of said stations of said anchor member, the 0.1 inch tube holder being located below the 0.15 inch tube holder.

17. The medical tubing anchor of claim 1, wherein said anchor member comprises two stations and three tube holders per station.

18. The medical tubing anchor of claim 1, wherein said anchor member comprises three stations and two tube holders per station.

19. The medical tubing anchor or claim 1, wherein said anchor member comprises four stations, two tube holders in three of said stations and one tube holder in one of said stations.

20. A method of anchoring a plurality of medical tubing to the body of a patient comprising the steps of:

providing:

a base support, said base support having an adhesive side and a non-adhesive side;

a flexible anchor member, said anchor member being a generally elongated rectangular solid having two elongated sides, two ends, a base, and a top;

said anchor base of said anchor member being mounted on said base support non-adhesive side;

said anchor member having a plurality of stations defined by passageways transversing said anchor member and extending from said anchor member top towards said anchor member base;

at least one tube holder having a generally cylindrical cross-section is located along said passageway in each of said stations for receiving medical tubing, said at least one tube holder extending from one elongated side to the other of said elongated sides; and a keeper on said anchor member for keeping medical tubing disposed in said stations from inadvertent release each of said at least one tube holder of each said station being capable of receiving separate medical tubing, whereby said medical tubing anchor anchors a plurality of medical tubing.

21. The method of claim 20 further comprising the steps of:

placing said adhesive side of said base support onto the body of a patient;

opening said keeper on said anchor member;

inserting at least one medical tube into an empty tube holder of said anchor member; and closing said keeper on said anchor member.

* * * * *